United States Patent [19]

Moreuil

[11] Patent Number: 4,508,733
[45] Date of Patent: Apr. 2, 1985

[54] DRUG FOR STIMULATING HEPATIC CELL HOMEOSTASIS AND FOR RESTORING THE FUNCTIONAL CAPACITY OF THE HEPATOCYTES

[75] Inventor: René Moreuil, Paris, France

[73] Assignee: Arconthorn Limited, London, England

[21] Appl. No.: 439,181

[22] Filed: Nov. 4, 1982

[51] Int. Cl.³ .................. A61K 31/185; C07C 143/02
[52] U.S. Cl. ............................... 514/578; 260/513 N
[58] Field of Search .................... 424/315; 260/513 N

[56] References Cited

U.S. PATENT DOCUMENTS 3,530,179 9/1970 Banci et al. .................... 260/513 N Primary Examiner—Alan Siegel
Attorney, Agent, or Firm—Birch, Stewart, Kolasch & Birch

[57] ABSTRACT

A drug is described which is constituted by aminoethanethiosulphonic acid

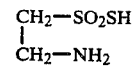

which can effectively stimulate hepatic cell homeostasis and restore the functional capacity of the hepatocytes.

4 Claims, No Drawings

DRUG FOR STIMULATING HEPATIC CELL HOMEOSTASIS AND FOR RESTORING THE FUNCTIONAL CAPACITY OF THE HEPATOCYTES

The present invention relates to a drug which can effectively stimulate hepatic cell homeostasis and which can equally effectively restore the functional capacity of the hepatocytes by acting essentially as an enzymatic activator and inducer.

It is known that there is constant, intense pharmacological research into identifying new and effective remedies for all those metabolic disorders which are occurring ever more frequently and which are essentially and fundamentally correlated with nutritional errors, the presence of toxic substances in the environment and a reduced capacity for maintaining the optimum desired levels of homeostasis of metabolic activities.

It is equally well known that several drugs have resulted from the present pharmacological research and have been published, which, even though this research has taken numerous different paths, and although they are satisfactory from various points of view, all have disadvantages which cannot be neglected and have not been overcome, such as for example, side effects, contra-indications, poor assimilability, if not absolute rejection in certain cases and, not least, accumulation in the human body.

The main object of this invention is to provide a drug which, acting on the liver, is effective in stimulating hepatic cell homeostasis and in restoring the functional capacity of the hepatocytes, while simultaneously overcoming all the disadvantages mentioned above with reference to the drugs of the known art.

This, and other objects, are achieved by a drug constituted essentially by aminoethanethiosulphonic acid, having the formula

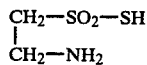

Aminoethanethiosulphonic acid, which is a physiological molecule, that is to say, a molecule present in the human and animal body, is a white, crystalline powder which is soluble in water, has a melting point of 213°–215° C., and considerable stability in the solid state even at 50° C. for very long periods of time. The effectiveness of the action of aminoethanethiosulphonic acid on hepatocytes, which will be seen from the documented tests given below in this specification, is basically due to the simultaneous presence in its structural formula of an —SH radical and an —SO₂ radical, as well as to its being a physiological molecule. It should be noted that, to the knowledge of the Applicant, no other molecule used up till now in therapy can claim the simultaneous presence of these radicals.

The importance of these radicals is evidenced by the fact that, as is well known, —SH radicals can fulfil the following functions:

they prevent, retard or oppose lipoperoxidation of mitochondria and microsomes. Lipoperoxidation selectively attacks fatty acids with multiple unsaturation, particularly those present in the membranes of mitochondria, microsomes and all the hepatocytes.

they are powerful enzymatic inducers towards all those enzymes which contain —SH radicals, among which, in particular, are glutathione, coenzyme A, hexokynase, L.D.H. and succinic acid dehydrogenase.

when administered to mammals, they are able to increase the hydrosulphide radical content of the tissue proteins, these radicals being a key element in the metabolic activity of the proteins themselves.

they can combine with various toxic substances, in particular liver-damaging substances, preparing them for neutralization and elimination.

With regard to the —SO₂ radical, the effectiveness of its protective action, again on the liver, as well as its effective anti-toxic action and its importance in sulphonation processes have been known for some time. It is convenient to note, with regard to lipid metabolism, that cholesterol is converted into cholic acid in the liver before combining with glycine and taurine, and is then excreted with the bile. It is well known that the esterification of cholesterol and, consequently, the esterified cholesterol/free cholesterol ratio, is influenced by the presence of —SH radicals. The availability of free fatty acids is also influenced by the presence of these radicals.

The present invention also relates to a method for preparing aminoethanethiosulphonic acid which consists essentially of the successive steps of:

sulphochlorination of phthalimidoethanol to obtain phthalimidoethane sulphochloride, having the structural formula:

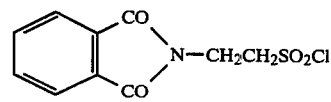

treatment of phthalimidoethane sulphochloride under hot conditions with phenylhydrazine and subsequently with tributylamine to obtain a solution from which there is precipitated, by cooling, a product constituted by aminoethanesulphinic acid having the formula:

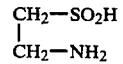

heating the aminoethanesulphinic acid recovered from the said solution under reflux with sulphur in alcoholic solution in the presence of a strong base and under agitation to obtain a product constituted by aminoethanethiosulphonic acid having the formula:

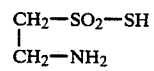

recovering the said aminoethanethiosulphonic acid by filtration and subsequent drying.

Further characteristics of the invention will become clearer from the following embodiment of a method for preparing aminoethanethiosulphonic acid and from the subsequent data taken from a whole series of experiments carried out on the aminoethanethiosulphonic acid which constitutes the drug of this invention.

EXAMPLE 76 g of phthalic anhydride are added gradually, under agitation, to 31 g of ethanolamine, the addition being controlled to prevent the exothermic reaction from becoming too violent. On completion of this addition, the solution is heated to 200° C. for 30 minutes. After cooling, a solid product is obtained which consists of phthalimidoethanol having the formula:

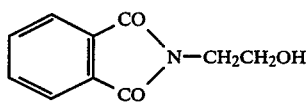

This product is dried under vacuum and ground (yield about 100 g)

120 g of the phthalimidoethanol obtained are added, under agitation, to 220 ml of thionyl chloride in a controlled manner to avoid too energetic a reaction. The solution is heated gradually under reflux and maintained under these conditions for 5 hours before the excess thionyl chloride is distilled off. A syrupy residue is obtained which is taken up with ice, filtered, washed and dried. The product obtained, crystallized from ethyl alcohol (yield 125-135 g), is constituted by phthalimidochlorethane, melting point 84°-88° C., having the formula:

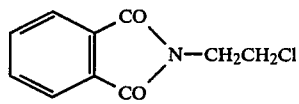

130 g of sodium sulphide in 250 ml of ethyl alcohol were heated under reflux and subsequently 15 g of sulphur were added under agitation and heated under reflux until the sulphur had completely dissolved. To this solution were then added 135 g of phthalimidochlorethane dissolved in 150 ml of ethanol. The solution was heated for a further 3 hours. The solution was then concentrated to dryness and the dry residue was taken up in 400 ml of acetic acid and 100 ml of water. Chlorine gas was bubbled slowly through the solution obtained at ambient temperature until no further absorption occurred. Thus a product was obtained which was constituted by phthalimidoethane sulphochloride having the formula:

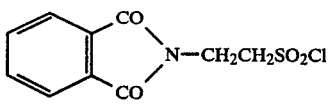

28 g of this sulphochloride, 30 g of phenylhydrazine and 100 ml of ethanol were heated under reflux to obtain a suspension which was initially very dense and difficult to agitate. This suspension then tended to fluidify. Immediately after the suspension has reached a certain degree of fluidity, 25 ml of tributylamine were added to it and the mixture was heated under reflux for 15 hours. Gradually the suspension dissolved completely and subsequently a product was precipitated. 300 ml of hot methyl ethyl ketone and then 6 ml of cold citric acid were added, agitation being maintained for several hours. Subsequently, after filtration, the filtrate was washed with methyl ethyl ketone and then with methanol and then dried. The product obtained, with a yield of 15-18 g, was aminoethanesulphinic acid having the formula:

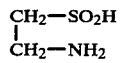

120 g of the aminoethanesulphinic acid thus obtained, 540 ml of 2N caustic soda and 37 g of sulphur in 5.5 l of ethanol were heated under reflux for 3 hours under agitation. After filtration while hot and subsequent cooling in a refrigerator for 15-20 hours, a product separated which consisted of aminoethanethiosulphonic acid having the formula:

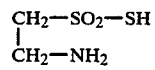

The filtered, dried product obtained, with a yield of 110-120 g, was crystallized from 1:1 alcohol-water, 70-80 g of pure product being obtained with a melting point of 213°-215° C.

The product is soluble in water. Its —SH titre is 98-99%, measured in accordance with Acta Chemical Scand 7,1137 (1953).

The aminoethanethiosulphonic acid, which constitutes the drug of this invention was tested experimentally on female Wistar rats to establish its antidyslipaemic effect in comparison with drugs already in use therapeutically. For this experiment, the rats were divided into five groups of five rats which were fed in accordance with the following scheme:

GROUP "A": rats fed with a normal diet of nutritive pellets having the following composition:

| Composition of the nutritive pellets: | |
| --- | --- |
| dry weight of crude proteins | 28.5% |
| dry weight of crude fiber | 7.5% |
| dry weight of crude lipids | 5.0% |
| crude ash | 8.5% |
| dry weight of non-nitrogenous extracts | 50.5% | with the addition of vitamins (A-$D_3$-E-C), NaCl, $CaCO_3$ and spring water as desired.

Group "B": rats fed with Nath diet (Nath et al. 1959—Journal of Nutrition, 67-289).

GROUP "C": rats fed with a Nath diet incorporating the drug tiadenol (1.25 g/kg) such that the rats could take up the drug in quantities of 100 mg/kg/day.

Group "D": rats fed with a Nath diet incorporating the drug of the invention (1.25 g/kg of aminoethanethiosulphonic acid) such that the rats could take up the drug in quantities of 100 mg/kg/day.

GROUP "E": rats fed with a Nath diet incorporating the drug of the invention (aminoethanethiosulphonic acid) in quantities of 2.5 g/kg, so that the rats could take up the drug in quantities of 200 mg/kg/day.

The experiments were carried out over a period of 45 days. On the 28th day of treatment, the cholesteraemia and the blood triglyceride level of the rats were measured.

On the 45th day from the start of the treatment, however, a whole series of systematic weight and hematochemical evaluations were carried out in accordance with the following scheme:

liver weight/body weight percentage ratio ratio of the weight of the liver when removed/dry weight of the liver cholesteraemia according to the Watson method (1)
1. WATSON D. (1960) Clin. Chim. Acta, 5: 637 blood triglyceride level according to the Bergmryer method (2)
2. BERGMRYER H. U. (1975) Z. Klin. Chem. and Klin. Biochem.13: 507 blood alkaline phosphatase level (3,4)
3. Anon. (1970) Z. Klin. Chem. and Klin. Biochem 13: 507.
4. Anon. (1972) Z. Klin.Chem. and Klin. Biochem 13: 507.

glutamic oxaloacetic transaminase level according to the Karmen method (5,6)
5. KARMEN A. and coll. (1955) J. Clin. Invest. 34: 126
6. KARMEN A. (1955) J. Clin.Invest. 34: 131 glutamic pyruvic transaminase level according to the Wroblewski and La-Due method (7)
7. WROBLEWSKI F. and coll. (1956) Proc.Soc. exp. Biol. Med. 91: 569.

total lipid content of the liver by extraction with ether, separation by decantation, evaporation of the ether part in an oven and weighing of the residue.

Macroscopic and microscopic, anatomical-pathological examinations of the liver and of the thoracic aorta were carried out on all the animals, the microscopic examinations being carried out by means of preservation in formalin, enclosure and coloration with hematoxylineosin and selective dyes for the lipids according to the current methods. The results of the hematochemical evaluations carried out on all the groups of rats on the 28th day of treatment are given in Table 1 below, while Table 2 shows the results of the weight and hematochemical evaluations carried out on the groups of rats on the 45th day of treatment.

From the data in Table 1 it is clear that the blood triglyceride and cholesterol levels in rats treated with a dose of 10 mg/kg/day of aminoethanethiosulphonic acid were noticeably less than those in rats kept on solely the Nath diet (31 and 129 mg% against 143 and 298 mg% respectively) and also less than those in rats fed with the Nath diet incorporating tiadenol (44 and 155 mg%).

The administration of aminoethanethiosulphonic acid in doses of 200 mg/kg/day does not, however, show any protective effect, still with reference to the blood triglyceride and cholesterol levels.

With reference to the variations in the weight parameters (percentage ratio of liver weight/body weight of the liver) and hemato-chemical parameters (cholesteraemia, triglyceridemia, blood alkaline phosphatase, blood transaminases and total lipid content of the liver) the following may be noted (Table 2):

compared with the control animals, the increase in the hepatic lipid infiltration encountered in rats maintained on a Nath diet was 235%, and this increase was reduced by half (117%) in rats which received aminoethanethiosulphonic acid in doses of 100 mg/kg/day in addition to their Nath diet; this protection was better than that given by thiadenol (+144%);

The levels of glutamic oxaloacetic transaminase (GOT) and pyruvic transaminase (GPT) increased by 109 and 60% respectively with the Nath diet; in rats protected by aminoethanethiosulphonic acid (100 mg/kg/day) the increase was 23 and 90% respectively. In rats having tiadenol added to their diet, the increases in GOT were 32% and in GPT were 100% compared with the controls (GROUP "A");

as regards the data on the cholesteraemia and on the blood triglycerides, there were considerable improvements as a result of the treatment with aminoethanethiosulphonic acid (100 mg/kg/day) on the 28th day, but on the 45th day they were not significantly better except in rats which had received the drug of the invention in doses of 200 mg/kg/day.

With regard to the macroscopic and microscopic anatomical-pathological studies carried out on dead rats on the 45th day of treatment, the following comments can be made:

examination of the thoracic aortas did not reveal significant pathological changes in any group of rats;

TABLE 1

Mean values of several parameters on the 28th day of treatment

| GROUPS | | TRIGLYCERI-DEMIA mg % | CHOLESTERAFMIA mg % | TOTAL LIPID CONTENT OF THE LIVER mg/g |
|---|---|---|---|---|
| A | CONTROLS | 93 | 48 | 60 |
| B | NATH DIET | 143 | 298 | 180 (+200%) |
| C | NATH DIET + TIADENOL(100 mg/kg/day) | 44 | 155 | 100 (+55%) |
| D | NATH DIET + AMINOETHANE-THIOSULPHONIC ACID (100 mg/kg/day) | 31 | 129 | 85 (+23%) |
| E | NATH DIET + AMINOETHANE-THIOSULPHONIC ACID (200 mg/kg/day) | 300 | 229 | 180 (+200%) |

TABLE 2

Percentage variation of the various parameters on the 45th day of treatment
The controls were put equal to 100

| LOTTO | 100 | LIVER WEIGHT BODY WEIGHT | TOTAL LIVER WEIGHT DRY LIVER WEIGHT | CHO-LES-TEROL | TRI-GLYC-ERIDES | ALKA-LINE PHOS-PHATASE | GOT | GPT | LIVER LIPIDS |
|---|---|---|---|---|---|---|---|---|---|
| B | | 146% | 138% | 535% | 203% | 133% | 160% | 209% | 335% |
| C | | 128% | 107% | 333% | 164% | 214% | 132% | 200% | 244% |
| D | | 147% | 107% | 368% | 226% | 272% | 123% | 190% | 217% |
| E | | 142% | 126% | 376% | 159% | 185% | 296% | 422% | 473% | in rats treated solely with a Nath diet, hepatic steatosis was not massive but was nevertheless considerable; the greater proportion of rats treated with aminoethanethiosulphonic acid did not, however, show hepatic steatosis and a similar comment could be made on rats treated with tiadenol (100 mg/kg/day).

Experiments were carried out in the same manner as explained above with other drugs presently in use and, more particularly, phosphorylcholine (2 doses/25 and 50 mg/kg), sillimarine (Legalon, 70 mg/kg), and S-adenosyl-1-methionine (Samyr) 25 mg/kg.

From the entire data found from these experiments and their comparison with the data found from experiments carried out with the drug of this invention (aminoethanethiosulphonic acid), it may be noted that:

the simultaneous administration of the drug of this invention with the Nath diet (100 and 200 mg/kg/day respectively), and particularly the dosage of 100 mg/kg/day, significantly reduces the increase in triglyceridemia on the 25th and 35th day of administration. In percentage terms, the triglyceridemia does not increase by the 25th day and increases only by 15% and 40% respectively by the 35th day. In rats fed solely with the Nath diet, the increase is, however, 100%. Among the control drugs, only phosphorylcholine (50 mg/kg) achieves a slight reduction ($-20\%$) relative to the increase observed at the end of the period with the aetherogenic diet.

as regards the cholesteraemia, the protective action shown by the drug of the invention was significant. Indeed, in rats fed with the drug phosphorylcholine, a 300% increase was found after 25 days and 320% and 410% increases respectively were found on the 35th and 45th days of feeding, while in rats fed with aminoethanethiosulphonic acid (100 mg/kg) the increase in cholesteraemia was only 35% on the 25th and on the 35th days. On the 45th day the increase was 50%.

Among the control drugs, a certain protective action, again noticeably less than that produced by aminoethanethiosulphonic acid, was shown by the Legalon and the Samyr.

The changes in the transaminase levels (GOT and GPT) also showed that the drug of the invention (aminoethanethiosulphonic acid) has a good antiatherogenic and liver protective action particularly at the dosage of 100 mg/kg. The protection offered by conventional drugs was, however, negligible with the exception of the Samyr which showed a certain favorable action on the 35th day of administration.

The data observed on the level of hepatic parenchyma, relative to the infiltration of fat resulting from the Nath diet are also notable. The increase in the quantity of lipids in the tissue ($+155$ and $+225$ respectively on the 25th and 45th days of administration) observed in rats kept on the Nath diet was reduced to 50% and 98% of this increase in rats which received 100 mg/kg of aminoethanethiosulphonic acid in addition to the Nath diet. In rats fed with the Nath diet incorporating 200 mg/kg of the drug of the invention the increase was 95% and 110% respectively on the 25th and the 45th day of administration. For the control drugs, phosphorylcholine, Lagalon and Samyr, protection was found but was only half that given by the aminoethanethiosulphonic acid, still from the point of view of lipid infiltration.

Experiments were carried out on the activity of the drug of this invention on liver damage in rats induced by allyl alcohol. This damage was evaluated by means of the weight of the liver, the quantity of lipids in the tissue itself and the excretion of BSP in the bile, as well as the changes in the GOT, GPT and the alkaline phosphatase levels in the blood.

The data noted from the experiments are given in Table III below. The respective administrations to the rats were carried out intraperitoneally for 4 days. From the data in Table III it is seen that the weight of the rats' livers increased from 5.03 mg to 6.06 mg in rats poisoned with allyl alcohol, while the increase was only up to 5.30 mg in rats fed intraperitoneally with allyl alcohol and aminoethanethiosulphonic acid (drug of the invention). When allyl alcohol and the drug known the by name Thiola (100 mg/kg/day) was administered to the rats, the liver weight increased to about 5.85 mg.

With regard to the increase in the total lipid content of the liver, from 4.98 mmg% in the controls to 5.23 mmg% after allyl alcohol, the drug of the invention showed that it could limit this increase to 5.08 mg% while the drug Thiola did not give any protection. The results of the determinations on the changes in the transaminase levels were equally significant.

Table IV below gives data relative to the protection offered by the administration of aminoethanethiosulphonic acid (100 mg/kg/day) and a control drug (phosphorylcholine, 50 mg/kg/day) to groups of Wistar rats subjected to two different atherogenic diets, specifically the Morris diet and the Handler diet, for 45 days. The data, in general, substantially repeated those observed in experiments carried out on animals subjected to the Nath diet.

TABLE III

Activity against liver damage in rats induced by allyalcohol
The allyalcohol was administered (2 ml/kg/ p.o. in a 2% physiological solution) 30 minutes after the last administration of the substance to be tested.

| TREATMENT | DOSE mg/kg/day for 4 days | LIVER Weight mg | Lipids Tot. mg % | SERUM BSP γ/ml | GOT mU/ml | GPT mU/ml | ALKALINE PHOSPHATASE U/ml |
|---|---|---|---|---|---|---|---|
| CONTROL | — | 5.03 ± 0.15 | 4.98 ± 0.28 | 14.1 ± 1.7 | 141.4 ± 6.0 | 9.24 ± 0.7 | 3.01 ± 0.24 |
| ALLYL ALCOHOL | — | 6.06 ± 0.24 | 5.23 ± 0.28 | 43.4 ± 11.3 | 638.3 ± 77.9 | 185.5 ± 38.7 | 3.53 ± 0.48 |
| ALLYL ALCOHOL + (XX)* | 100 i.p. | 5.30 ±0.05 | 5.08 ±0.39 | 12.31 ±0.91 | 172.0 ±10.2 | 25.9 ±2.5 | 2.40* ±0.10 |
| ALLYL ALCOHOL + THIOL | 100 i.p. | 5.95 ± 0.25 | 5.23 ± 0.30 | 21.78 ± 2.99 | 388.0 ± 25.8 | 99.4 ± 12.2 | 3.13 ± 0.23 |

*(XX) = aminoethane thiosulphonic acid

TABLE IV

| CONTROLS | TRIGLYCERI-DEMIA 100 | CHOLESTER-AEMIA 100 | TOTAL BLOOD LIPIDS 100 | BETALIPOPROTEINS 100 | HEPATIC LIPIDS 100 |
|---|---|---|---|---|---|
| WISTAR RATS KEPT ON A MORRIS DIET FOR 45 DAYS | | | | | |
| MORRIS DIET | — | +195% | +230% | +210% | +145% |
| MORRIS DIET (XX)* 100 mg/kg | — | +70% (60% protection) | +175% (40% protection) | +155% (45% protection) | +73% (50% protection) |
| MORRIS DIET + PHOSPHORYLCHOLINE 50 mg/Kg | — | +165% (12% protection) | +210% (5% protection) | +190% (8% protection) | +125% (12% protection) |
| HANDLER DIET | +90% | +380% | +215% | — | +168% |
| HANDLER DIET (XX)* 100 mg/kg | +63% (30% protection) | +230% (35% protection) | +160% (33% protection) | — | +88% (50% protection) |
| HANDLER DIET + PHOSPHORYL-CHOLINE 50 mg/Kg | +83% (7% protection) | +330% (15% protection) | +198% (10% protection) | — | +130% (23% protection) |
| WISTAR RATS ON A HANDLER DIET FOR 45 DAYS | | | | | |

*(XX) = aminoethanethiosulphonic acid

From the Table it can be seen that the protection offered by aminoethanethiosulphonic acid was significant; on the blood, where the increase in cholesteraemia was notably lower: an average reduction to 60% of the increase registered among rats kept on the Morris diet, while the increase was kept to 35% for those on the Handler diet. For the phosphorylcholine, the reductions were only 12% and 15% respectively.

For the triglyceridemia the reduction was 30% after the Handler diet as against a reduction of only 7% with the use of phosphorylcholine.

The blood lipid content was reduced to 40% among rats kept on a Morris diet and to 33% after the Handler diet; with the administration of phosphorylcholine these values were 5% and 10% respectively less than those observed in rats kept on the two atherogenic diets.

For the beta lipoproteins, the protection observed was 45% against a protection of 8% obtained with the phosphorylcholine, still after the Morris diet.

Finally, lipid infiltration into the liver increased by only 50% in rats protected with aminoethanethiosulphonic acid compared with those kept on the Morris and Nath diets.

The effectiveness of the action of the drug of this invention (aminoethanethiosulphonic acid) on hepatocytes was further supported by tests on poisoning with heavy metals and carbon tetrachloride. Sulphobromophthalein tests also showed the effectiveness of the protective action exerted by the drug of the invention on Wistar rats subjected to poisoning with carbon tetrachloride or an atherogenic diet.

From the toxicological point of view, the administration of aminoethanethiosulphonic acid did not result in any increase in mortality nor any variation in the weight curve even when the administration was kept up for 180 days with a daily dose of 200 mg/kg of body weight.

What is claimed is:

1. A method for stimulating hepatic cell homeostasis which comprises administering to a host an effective amount of aminoethanethiosulphonic acid having the formula:

$$\begin{array}{l} CH_2-SO_2SH \\ | \\ CH_2-NH_2 \end{array}$$

or a pharmaceutically acceptable salt thereof.

2. A method for restoring the functional capacity of hepatocytes which comprises administering to a host an effective amount of aminoethanethiosulphonic acid having the formula:

$$\begin{array}{l} CH_2-SO_2SH \\ | \\ CH_2-NH_2 \end{array}$$

or a pharmaceutically acceptable salt thereof.

3. A method for stimulating hepatic cell homeostasis and for restoring the functional capacity of hepatocytes which comprises administering to a host an effective amount of aminoethanethiosulphonic acid having the formula:

$$\begin{array}{l} CH_2-SO_2SH \\ | \\ CH_2-NH_2 \end{array}$$

or a pharmaceutically acceptable salt thereof.

4. A method for stimulating hepatic cell homeostasis and for restoring the functional capacity of hepatocytes which comprises administering to a host an effective amount of crystalline aminoethanesulphonic acid having the formula:

$$\begin{array}{l} CH_2-SO_2SH \\ | \\ CH_2NH_2 \end{array}$$

and having a melting point of 213° to 215° C. or a pharmaceutically acceptable salt thereof.

* * * * *